(12) United States Patent
Ogasawara et al.

(10) Patent No.: US 6,416,476 B1
(45) Date of Patent: Jul. 9, 2002

(54) THREE-DIMENSIONAL ULTRASONIC DIAGNOSIS APPARATUS

(75) Inventors: Yoichi Ogasawara; Ryoichi Kanda, both of Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/481,526

(22) Filed: Jan. 12, 2000

(30) Foreign Application Priority Data

Jan. 12, 1999 (JP) .......................................... 11-005687

(51) Int. Cl.[7] ................................................ A61B 8/00
(52) U.S. Cl. ........................ 600/443; 600/425; 600/437
(58) Field of Search ................................ 600/437, 443, 600/439, 425, 426, 429, 436, 407

(56) References Cited

U.S. PATENT DOCUMENTS 5,129,397 A * 7/1992 Jingu et al. ................. 600/437
5,261,404 A * 11/1993 Mick et al. ................. 600/425
5,823,958 A * 10/1998 Truppe ....................... 600/426

* cited by examiner

Primary Examiner—Marvin M. Lateef
Assistant Examiner—Ruby Jain
(74) Attorney, Agent, or Firm—Oblon, Spivak, McClelland, Maier & Neustadt, P.C.

(57) ABSTRACT

A three-dimensional ultrasonic diagnosis apparatus transmits ultrasonic beams to an object; receives ultrasonic echo signals; stores and generates three-dimensional region volume data in an object OB based on ultrasonic echo signals; detects direction data concerning an orientation of an operator's head part; and generates and displays the two-dimensional display image from volume data in real time based on the detected direction data. This apparatus provides the three-dimensional anatomical information on the field of interest seen from the operator's viewpoint automatically; assists smooth operation; and reduces a burden of an inspector or an operator that is also an inspector during operation upon ultrasonic beams scanning.

15 Claims, 11 Drawing Sheets

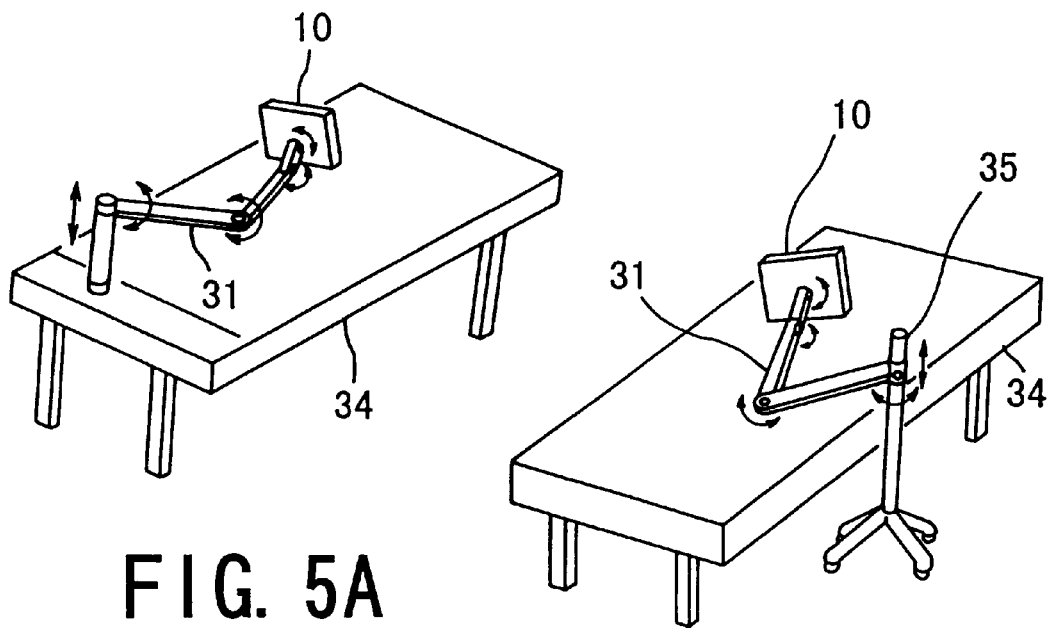
FIG. 5A
FIG. 5B
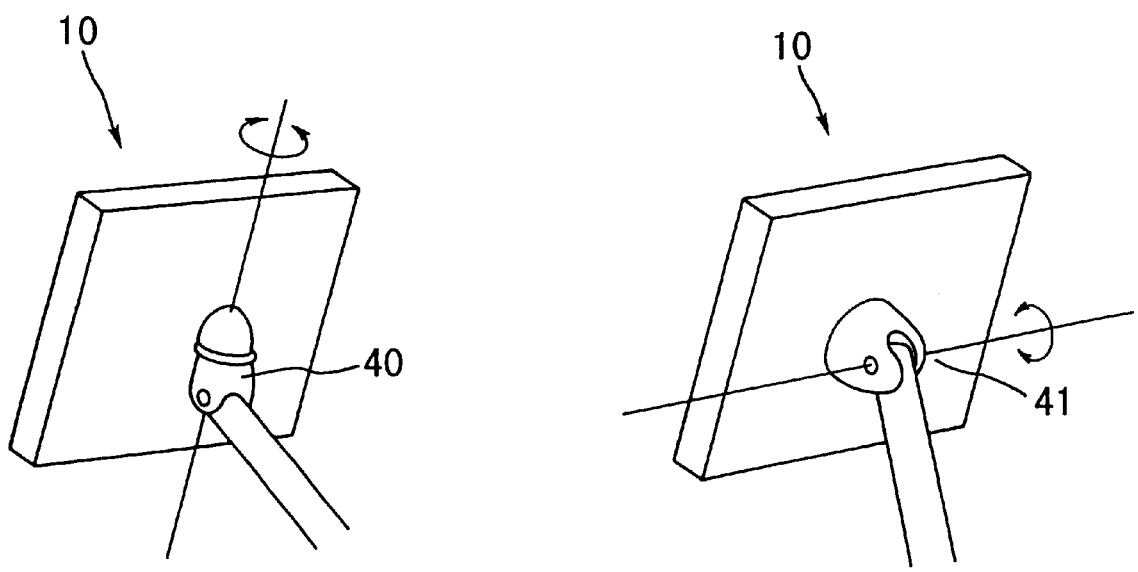
FIG. 6A
FIG. 6B

THREE-DIMENSIONAL ULTRASONIC DIAGNOSIS APPARATUS

BACKGROUND OF THE INVENTION

The present invention relates to a three-dimensional ultrasonic diagnosis apparatus for displaying a three-dimensional (3D) image in real time. In particular, the present invention relates to a 3D ultrasonic diagnosis apparatus for displaying a 3D image suitable to intra-operative assistance.

In general, a two-dimensional (2D) ultrasonic diagnosis apparatus for displaying a tomographic image by scanning ultrasonic beams in a single plane is known. In recent years, in this 2D ultrasonic diagnosis apparatus, there is actively made an attempt for acquiring a 3D image for an object to be diagnosed and displaying the image. Such a technique for displaying the 3D image is greatly expected to open up the possibility of intra-operative The changes being made to the specification are shown using underlining and bracketing in the attachment hereto.

It is known that such 2D ultrasonic diagnosis apparatus for acquiring such kind of 3D information collects a diagnostic image while moving a one-dimensional (1D) array probe as an ultrasonic transducer (probe) configuring a transmission/receiving section of ultrasonic beams. In this case, there is studied that a convex probe or linear probe for an abdominal region is employed as a 1D array probe to manually or mechanically move the probe or that an esophageal multi-plane probe is employed to rotate its electronic sector probe.

However, acquiring 3D information employing a 1D array probe itself requires considerably more time than conventional tomographic scanning. Therefore, there has been a problem that, in the case of an object with fast movement, such as a heart, motion information cannot be traced. Even in the case where a probe is not fully fixed to an abdominal region with a movement that is not faster than that of the heart, an image is considerably distorted.

Moreover, when intra-operative assistance is performed by employing 3D information acquired by such 1D array probe, an image displayed on a monitor is a 2D tomographic image in a scanning face of a 1D array probe. Thus, during operation, an operator in chief (hereinafter, referred to as an "operator") or an inspector must grasp three-dimensional anatomical information on an object of surgery (hereinafter, referred to as a "field of interest", "target site" or the like) while observing the 2D anatomical information. That is, an operator or inspector acquires a plurality of tomographic images by moving the scanning face of the 1D array probe during operation, and virtually integrates and constructs its probe operation position, an image acquired at that position, and anatomical knowledge in his or her mind, thereby making it necessary to visualize the anatomical information on a target site of the object. Therefore, if the operator and the inspector are different from each other, mutual thorough communication during operation is required. In addition, the inspector is always required to have further highly skilled ultrasonic probe handling technique, and thus, it is not always effective.

SUMMARY OF THE INVENTION

The present invention has been achieved in view of this conventional problem. It is an object of the present invention to provide a three-dimensional ultrasonic diagnosis apparatus for reducing the burden of ultrasonic scanning upon an inspector or an operator acting as the inspector during an operation, by automatically providing 3D anatomical information of the field of interest viewed from the operator's viewpoint; thus assisting a smooth operation.

In order to achieve the foregoing object, according to the present invention, there is provided a three-dimensional diagnostic apparatus comprising: an ultrasonic probe for transmitting ultrasonic beams toward an object and receiving ultrasonic echo signals thereof; means for generating and storing three-dimensional region volume data from the patient based on the ultrasonic echo signals; direction detecting means for detecting direction data concerning an orientation of an operator's head or face part; and image display means for generating and displaying a two-dimensional display image from the volume data in real time based on the direction data outputted from the direction directing means.

In the present invention, the ultrasonic probe can be an 1D (one-dimensional array probe or a 2D array probe (two-dimensional phased array ultrasonic transducer). Preferably, the ultrasonic probe may be the 2D array probe.

The 2D array probe scans ultrasonic beams three-dimensionally, thereby making it possible to acquire and display a three-dimensional volume image. When intra-operative assistance is performed by using such three-dimensional volume image, volume data can be acquired by three-dimensionally scanning it by the 2D array probe, making it possible to acquire in real time three-dimensional information that could not be obtained in the 2D tomographic image using the 1D array probe. In this manner, the operator or inspector can observe a target site from an arbitrary point of view. Accordingly, in the 3D ultrasonic diagnosis apparatus using such 2D array probe, a request for the inspector's ultrasonic inspection technique becomes less necessary than the 2D ultrasonic diagnosis apparatus using the 1D array probe. Moreover, as the 2D array probe has been researched and developed considering intra-operative assistance in particular, the 3D display of the object's field of interest is effectively provided. As a result, in the 3D ultrasonic diagnosis apparatus, there can be obtained information effective to intra-operative assistance such as the view and position of a 3D-displayed site in the field of interest, and the position relation with respect to the operator.

In the present invention, the three-dimensional ultrasonic diagnosis apparatus can further comprise means for changing a magnification of the two-dimensional display image according to a change in distance between the head or face part of the operator and the three-dimensional region in the patient.

The direction detecting means comprises a first position sensor for detecting first position information concerning the viewpoint of the operator or a certain point in a certain position relation with the viewpoint of the operator; and a second position sensor for detecting second position information concerning the position of the ultrasonic probe. The image display means can comprise: view setting means for setting a view of the operator in real time based on the two-position information detected by the two position sensors; and a display portion for displaying three-dimensional anatomical information of the field of interest in real time when the three-dimensional volume information is seen from a view set by the view setting means.

The first sensor can be mounted on an intra-operative goggle or eyeglasses that the operator wears, and the second sensor can be mounted on the ultrasonic probe.

There can be further provided an arm device in which the display portion is movably installed on a region in the vicinity of the field of interest of the patient.

The arm device can comprise an arm main body and at least one joint section disposed at this arm main body, the joint section being rotary at least in horizontal and vertical direction.

The display portion can comprise a rotary rotation mechanism so as to automatically orient the display face to the operation side.

The display portion can further comprise means for controlling the rotation mechanism using position information from the first position sensor.

The display portion can be configured in the intra-operative goggle that the operator wears. The display portion configured in the intra-operative goggle can comprise ON/OFF control means for controlling display/non-display of an ultrasonic image by means of an ON/OFF function of a switch. The ON/OFF control means is capable of being means for controlling information concerning a normal field of interest to be displayed during non-display of the ultrasonic image.

In addition, in order to achieve the foregoing object, in another aspect of the present invention, there is provided a three-dimensional ultrasonic diagnosis apparatus comprising: an ultrasonic probe for transmitting ultrasonic beams to a patient and receiving ultrasonic echo signals; means for generating and storing three-dimensional region volume data in the patient based on the ultrasonic echo signals received by the ultrasonic probe; direction detecting means for detecting direction data concerning a viewing direction of an operator; and image display means for generating and displaying a two-dimensional display image from the volume data in read time based on the direction data outputted from the direction detecting means.

With the foregoing structure, the following advantageous effect can be obtained.

First, assume that a 2D ultrasonic system using a conventional 1D array probe is employed in intra-operative assistance. In this case, an ultrasonic image observed in the 2D ultrasonic system is not seen from the operator's viewpoint, but is a scanning cross section of the 1D array probe. Thus, it is inconvenient to know a relationship between vertical blood vessel structures or tissues based on the information only on the scanning cross section. In addition, the operator must move his or her view considerably to the ultrasonic system installed on a monitor in order to observe an ultrasonic image inside of the field of interest. Such changing the operator's view considerably could lead to degradation of the operator's work efficiency.

In contrast, assume that intra-operative assistance is performed using the 3D ultrasonic system according to the present invention. In this case, first, by a small-sized position sensor such as 3D magnetic sensor mounted on the goggle or eyeglasses that the operator wears, a position of the position sensor and the directional vector of the sensor at that position are detected as direction data concerning the orientation of the operator's head part. With image display means, from 3D data collected in real time by means of an ultrasonic probe such as 2D array probe based on the detected direction data, and a 3D image such as a VR (Volume Rendering) image or MIP (Maximum or Minimum Intensity Projections) image in the operator's viewing direction is displayed.

In this manner, a three-dimensional position relationship between the blood vessels or tissues of the field of interest that could not be provided in the conventional system can be visualized in real time. In addition, the information from the position from the operator's viewpoint position can be automatically provided. Therefore, in the present invention, the 3D structure of the field of interest can be automatically recognized from the operator's viewpoint by employing the above-mentioned means, thus making it possible to improve operative work efficiency.

From the foregoing, according to the present invention, the 3D ultrasonic image of the field of interest from the operator's viewpoint can be automatically provided, and there can be substantially reduce a burden due to complicated processing that the three-dimensional anatomy in blood vessel structures or tissues that has been conventionally indispensable is constructed in mind. At the same time, in the present invention, a position relationship between surgical instruments such as surgical knife or puncture needle, blood vessel structures, or tissues can be recognized in real time, and the improvement in work accuracy or its efficiency is expected.

In addition, in the present invention, a display device can installed as image display means very close to a target site so that the operator's view does not considerably changes as described above. For example, a thin, light-weighted display device such as liquid crystal can be installed very close to a target site by employing a long arm, or a specific goggle with position sensor capable of displaying an ultrasonic image can be utilized. Thus, installing the display portion at a position very close to the field of interest makes it possible to eliminate considerable movement of the operator's view in order to see the display portion and improve work efficiency more significantly.

Further, according to the present invention, the inspector manipulating an ultrasonic probe is not required to have highly skilled technique, and can be handle the probe easily.

BRIEF DESCRIPTION OF THE DRAWINGS

The accompanying drawing which are incorporated in and constitute a part of this specification, illustrate embodiments of the present invention and, together with the description, serve to explain the principles of the present invention; in which:

FIG. 5A and FIG. 5B are schematic perspective views each illustrating an example when a display portion and an arm section are mounted on a patient couch or its support base according to the present invention;

FIG. 6A and FIG. 6B are schematic perspective views each illustrating an example when an oscillating (movable) portion is installed on a back face of the display portion according to the present invention;

DESCRIPTION OF THE PREFERRED EMBODIMENTS

Hereinafter, preferred embodiments of a three-dimensional ultrasonic diagnosis apparatus according to the present invention will be described with reference to the accompanying drawings.

Figure 1:
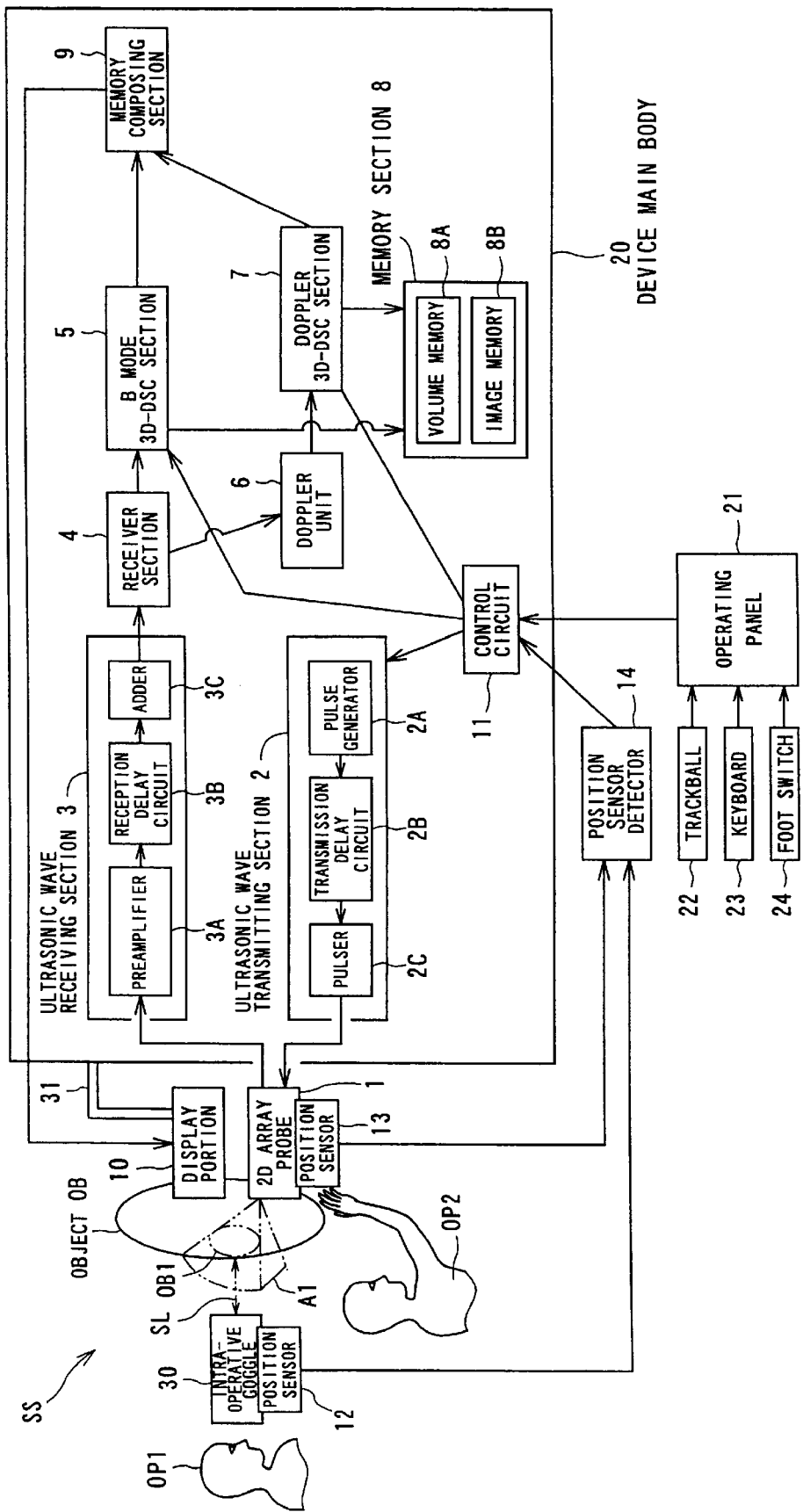
FIG. 1 is a block diagram depicting an embodiment of a three-dimensional ultrasonic diagnosis apparatus according to the present invention.

FIG. 1 shows an entire configuration of a three-dimensional ultrasonic diagnosis apparatus by way of embodiments. This three-dimensional ultrasonic diagnosis apparatus is applicable to intra-operative assistance. In this ultrasonic diagnosis apparatus, there is provided a 2D array ultrasonic probe 1 maintained to an inspector OP2 during operation by an operator (operator in chief OP1, the probe 1 transmitting/receiving an ultrasonic signal to/from a target site (diseased site or field of interest) OB1 of the patient (object) OB; a device main body 20 driving this ultrasonic probe 1 and processing its receiving signal; and an operating panel 21 for inputting an operating signal from the operator to this device main body 20.

The 2D array ultrasonic probe 1 is maintained by the inspector OP2 during operation in this example. The present invention is not limited thereto, and such probe may be maintained by the operator OP1 himself, for example, if it can be installed so that the field of interest OB1 required for the operator OP1 can be scanned, and may be mechanically fixed.

An input device such as trackball 22, keyboard 23, or foot switch 24 are connected independently to or are installed integrally on an operating panel 21, thereby making it possible for the operator to set the apparatus conditions using such input device, set to a ROI, and change a variety of these setting conditions.

The apparatus main body 2, as illustrated, comprises an ultrasonic wave transmitting section 2; an ultrasonic wave receiving section 3; a receiver section 4; a B mode 3D-DSC section 5; a Doppler unit 6; a Doppler 3D-DSC section 7; a memory section 8; a memory composing section 9; a display portion 10; a control circuit 11; and a position sensor detecting section 14.

Among them, the ultrasonic wave transmitting section 2, as illustrated, comprises a pulse generator 2A; a transmission delay circuit 2B, and a pulser 2C. This transmitting section 2 transmits a pulse generated at the pulse generator 2A to the pulser 2C via the delay circuit 2B, and drives the 2D array probe 1, thereby generating pulse-shaped ultrasonic beams and scanning the beams in a three-dimensional region A1 including the field of interest OB1 of the object OB. At this time, an ultrasonic echo signal with its narrower focus than that of the 1D array probe is obtained by performing focus point control for obtaining an echo signal. in an arbitrary direction of a space of the probe 1 by delay control of the delay circuit 2B; and sound field control in vertical direction to a tomographic image.

The ultrasonic wave receiving section 3, as illustrated, comprises a preamplifier 3A, a reception delay circuit 3B, and an adder 3C. This receiving section 3 captures an echo signal outputted by each channel from the probe 1; the preamplifier amplifies it at the preamplifier 3A every channel; the reception delay circuit 3B imparts a delay time required for determining reception directivity; and the adder 3C adds the time, thereby emphasizing a reflection component in a direction according to the reception directivity.

In the foregoing, the ultrasonic wave transmitting section 2 and the ultrasonic wave receiving section 3 control transmission directivity and reception directivity, thereby making it possible to form comprehensive ultrasonic beams while transmission and reception in the 2D array probe 1 are performed.

The receiver section 4 comprises a logarithmic amplifier (not shown) for receiving the echo signal from the ultrasonic wave receiving section 3; an envelope line wave detector circuit (not shown); an analog digital converter (an A/D converter) (not shown), and supplies its output to the B mode 3D digital scan converter (3D-DSC) section 5 via a volume memory 8A of the memory section 8 and a Doppler unit 6 as required.

The 3D-DSC section 5 performs processing for cutting out an arbitrary cross section of an image based on the 3D data recorded and maintained in the volume memory 8A of the memory section 8 or processing for causing mapping on a 2D plane from an arbitrary viewpoint using a predetermined 2D mapping technique; converts the processed data into a raster signal array of a video format, and send it to a memory composing section 9.

The Doppler unit 6 detects a Doppler signal in a Color Doppler technique based on the echo signal from the receiver section 4; calculates 3D information. such as speed, power, or variance; and sends the information to a Doppler 3D-DSC section 7 via the volume memory 8A of the memory section 8 in a similar manner as that in B mode.

The Doppler 3D-DSC section 7 performs processing for cutting out an arbitrary cross section of an image based on the 3D data recorded and maintained in the volume memory 8A of the memory section 8 or processing for causing mapping on the 2D plane from an arbitrary viewpoint using a predetermined 2D mapping technique, converts the processed data into a raster signal array of a video format; and sends it to the memory composing section 9.

The memory composing section 9 performs composing processing such as processing for listing and displaying information such as image or setting parameters or processing for displaying the information to be superimposed; and outputs the composed image as a video signal to a display portion 10. This display portion 10 displays a 3D-B mode image representative of 3D internal tissue shape of the object OB or 3D information (such as color blood flow information or flow speed information) of a Color Doppler (such as morphological information or gray scale image) superimposed thereon.

The memory section 8 has a volume memory 8A for recording and maintaining 3D information concerning the aforementioned B mode and copper Doppler and an image memory 8B for recording and maintaining the signal of each of the DSC sections 5 and 7 (any one or both of the 2D signal array mapped by the 3D-DSC section 7 and raster signal array of the video format). The information recorded and maintained in these volume memory 8A and image memory 8B is called by the operator during operation after diagnosis, and can be used.

The above 3D ultrasonic diagnosis apparatus incorporates an intra-operative assistance system SS in addition to the above construction. Hereinafter, this intra-operative assistance system SS will be described with reference to the accompanying drawings.

Figure 2:
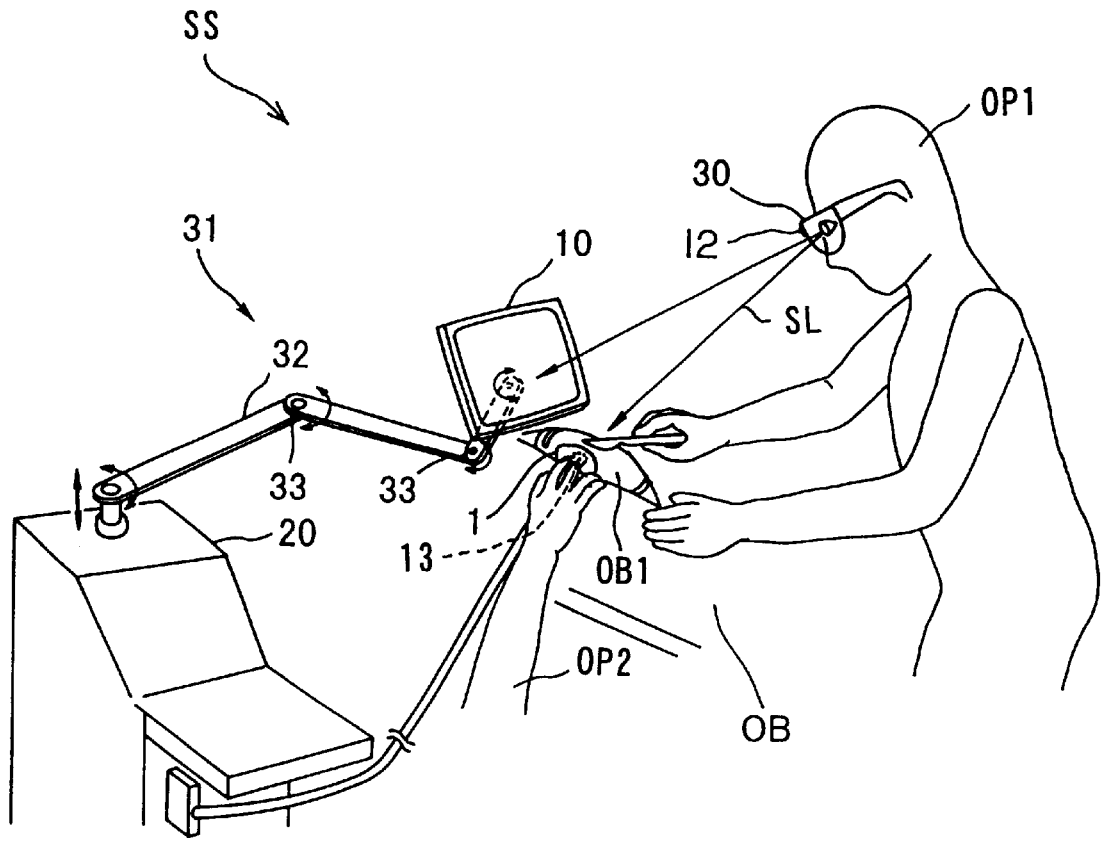
FIG. 2 is a schematic perspective view illustrating an example when the three-dimensional ultrasonic diagnosis apparatus according to the present invention is used during operation.
Figure 3:
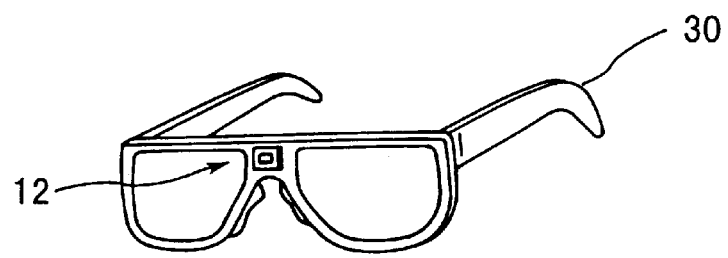
FIG. 3 is a schematic perspective view showing an intra-operative goggle with position sensor according to the present invention.

The intra-operative assistance system SS, as shown in FIG. 1 to FIG. 3, comprises: an intra-operative goggle (or eyeglasses) 30 that the operator OP1 can wear; a first position sensor 12 installed in this intra-operative goggle 30, the sensor detecting a predetermined position (for example, center) and direction of the goggle as information concerning the viewing direction of or the orientation of the head part of the operator OP1; and a second position sensor 13 for detecting a predetermined position (for example, two-dimensional array face) of the probe 1 and its direction.

In addition, this system SS comprises: a position sensor detecting section 14 for detecting the position vector and direction vector in a three-dimensional space with respect to the predetermined reference positions of both sensors 12 and 13 based on the detection signals from both of the position sensors 12 and 13 as shown in FIG. 1; a control circuit 11 for receiving the detection signals of the position vector and direction vector of both of the sensors 12 and 13 from this detecting section 14 and controlling each section in the apparatus main body 20 as required; and an arm section 31 installed between the apparatus main body 20 and the display portion 10 as shown in FIG. 2.

Each of the first and second position sensors 12 and 13 is composed of a 3D magnetic sensor for detecting a signal from a transmitter (a high-frequency coil) installed at a predetermined reference position in this example, thereby being capable of analyzing the three-dimensional position vector and direction vector with respect to the reference position. The present invention is not limited thereto, and is, of course, applicable to an element capable of detecting three-dimensional position information through predetermined electromagnetic waves or the like.

It is desirable that the first position sensor 12 is installed at the center of an intra-operative goggle 30 as shown in FIG. 3 in order to detect the viewing direction of and the orientation of the head part of the operator OP1. For example, even if this goggle is installed at an arbitrary slightly different position, the position vector and position vector can be software-compressed without impairment by means of a control circuit 11 after they have been detected by means of a position sensor detector 14. For similar reasons, the second position sensor 13 can be mounted at an arbitrary position free of impairment in operating the probe 1.

The position sensor detector 14 is connected to the output side of both position sensors 12 and 13, and the position vector and direction vector are always detected based on the detection signals from both of the sensors 12 and 13, and are sent to the control circuit 11.

Figure 4:
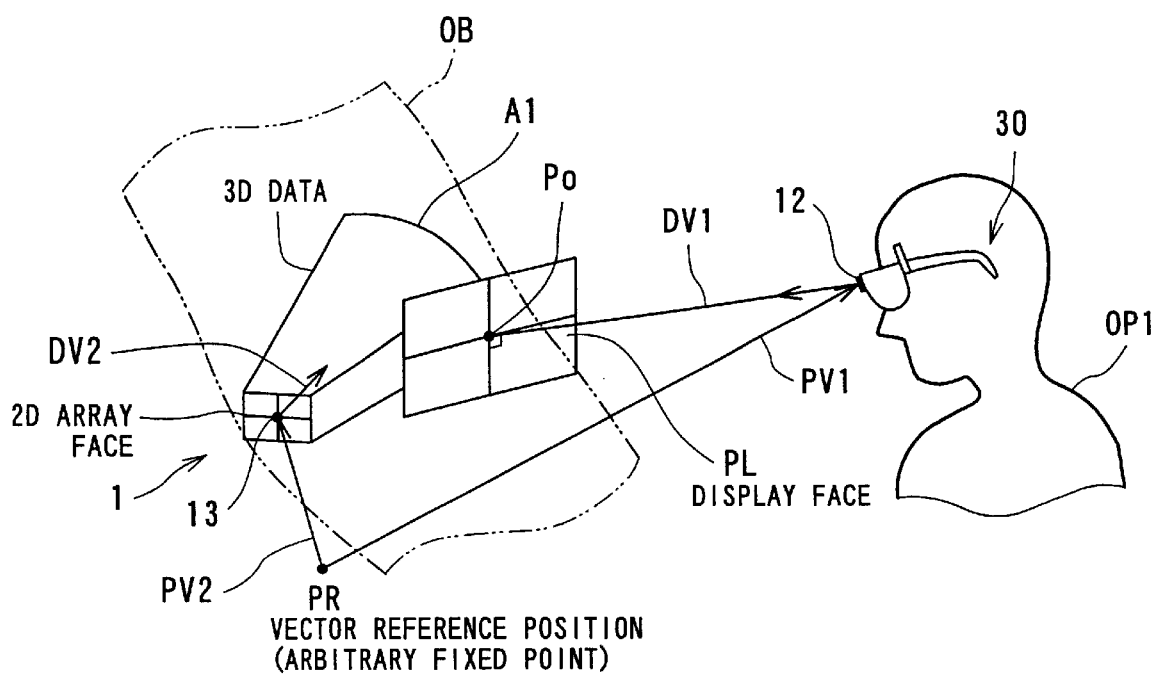
FIG. 4 is a conceptual view illustrating a relationship among a position sensor, a 3D scan area, and a 2D mapping face according to the present invention.

The control circuit 11 consists of essential portions of view setting means In in image display means of the present invention. As shown in FIG. 4, a spatial position of the 3D data in a 3D scan region A1 from the 2D array probe 1 with respect to the object of interest OB1 of the object OB is calculated based on the position vector PV2 and position vector DV2 with respect to the vector reference position PR of the second position sensor 12 detected by the position sensor detector 14.

At the same time, this control circuit 11, as shown in FIG. 4, employs the detected position vector PV1 and direction vector DV1 of the first position sensor 12 of the position sensor detector 14 to require the B mode 3D-DSC 5 and Doppler DSC 7 to set PL of a virtual face (hereinafter, "a 2D map" or "a display face") with its direction vector DV1 defined as a normal line; and to 2D-map and convert the 3D data in the 3D scan region A1 from a specific projection direction based on the direction vector to the display face PL.

The display face PL in which 2D mapping and conversion processing of 3D data is performed, as shown in FIG. 4, is a virtual face in which the direction vector DV1 is defined as a normal line from a terminal position (a goggle position) with respect to the reference position P0 of the position vector PV1 of the first position sensor 12 so as to be along a direction according to the viewing direction of or the orientation of the head part of the operator OP1, and a position crossing its normal line (a foot position of the perpendicular line) is set to be at the center (display reference position) P0 of the display face.

Two 3D-DSC 5 and 7 execute 2D mapping for 3D data collected in real time based on the request always sent from the control circuit 11, and converts the result into the raster signal array of the video format. The thus converted raster signal array is displayed in read time as a 3D image representative of the 3D tissue shape (anatomical information) of the field of interest OB1 of the object OB at the display portion 10 via the memory composing section 9.

That is, this real-time 3D image is produced as an image on which a 3D-B mode image of field of interest OB1 viewed in the viewing direction of the operator OP1 or in a specific direction based on the viewing direction or a Color Doppler image is superimposed.

This 2D image display area can be expanded and reduced by inputting the trackball 22, keyboard 23, foot switch 24 or the like. In addition, the information of the position vector and/or direction vector of both position sensors is inputted, thereby making it possible to change a magnification of a two-dimensional display image according to a distance variation between the head part of the operator OP1 and the three-dimensional region in the object OB.

The arm section 31, as shown in FIG. 2, comprises an arm main body 32 having a length such that a display portion 10 composed of a light-weight display device such as liquid crystal monitor can be disposed at a position extending from the apparatus main body 20, the position being very close to the field of interest of the object OB.

With this arrangement, the arm section 31 spatially moves an arm main body 32 via joint sections 33, . . . 33, universally in vertical or horizontal direction to adjust a predetermined height and orientation. In this manner, the display portion 10 is installed at a position very close to the field of interest, for example, at a proper position capable of being seen the field of interest and display portion 10 alternately merely by the operator OP lightly moving without oscillating the head.

Therefore, according to the illustrative embodiment, with this system employing a 3D ultrasonic diagnosis apparatus, a 3D ultrasonic image of the field of interest seen from the operator's viewpoint is automatically provided, thus making it possible to reduce a burden due to complicated processing in which the three-dimensional anatomy between the blood vessel structures or tissues which is conventionally required is constructed in mind.

In addition, according to the illustrative embodiment, a position relationship among surgical instruments such as surgical knife or puncture needle, blood vessel structures or tissues can be recognized in read time, and thus, improvement in work accuracy or efficiency can be expected.

Further, according to the illustrative embodiment, the display portion is installed at a position very close to the field of interest from the conventional apparatus main body, thereby making it unnecessary to considerably move the operator's view in order to see the display portion and improve work efficiency.

Furthermore, according to the illustrative embodiment, the inspector manipulating an ultrasonic probe can use it more simply without requiring highly skilled technique.

In the illustrative embodiment, the display portion 10 is connected to the apparatus main body 20 via the arm section 31; and however, the present invention is not limited thereto.

For example, the display portion 10 and arm 31 having the same functions as the above can be mounted on a patient couch 34, as shown in FIG. 5A, and is mountable to a support base 35 that can be installed at a predetermined position on the side of the patient couch 34, as shown in FIG. 5B.

In addition, at the display portion 10, as shown in FIGS. 6A and 6B, it is possible to mount a motor incorporated rotation mechanism 40 (horizontal rotation) automatically rotating (oscillating) on its back face (rear face) side so that a display face is provided at an angle that is the most visible for the operator OP1 in synchronism with an orientation of the intra-operative goggle in the control circuit based on the information (a position vector and a direction vector) acquired by a position sensor detector. It is desirable that a rotation function for the display face with this rotation mechanisms 40 and 41 is ON/OFF controlled by means of switch operation of the keyboard or foot switch (not shown).

Vertical and/or horizontal rotation may be applied to the above rotation mechanisms 40 and 41.

Figure 7:
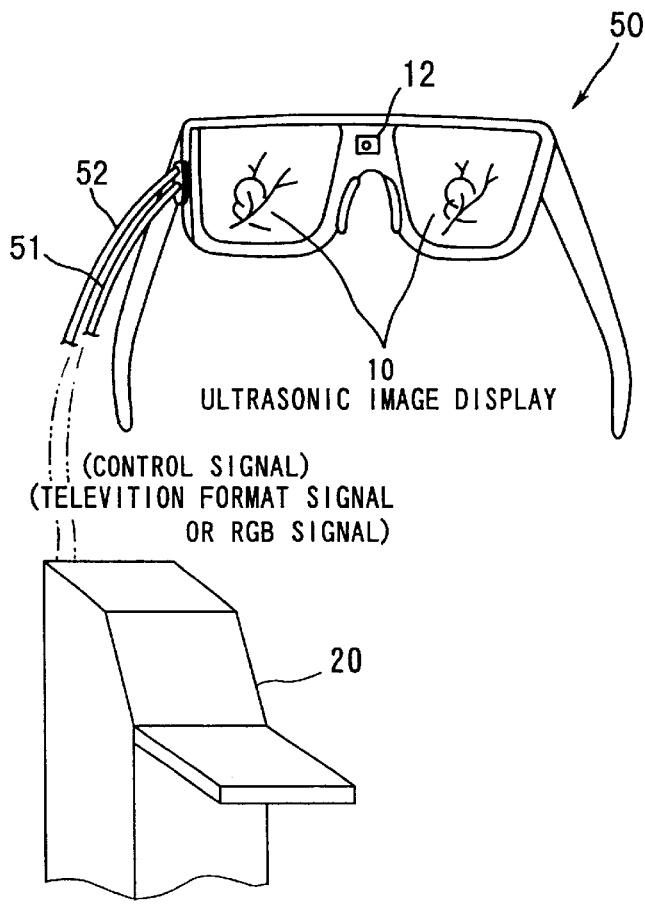
FIG. 7 is a schematic view showing an intra-operative specific goggle incorporated in the display portion according to the present invention.

As shown in FIG. 7, a specific goggle 50 incorporated in an ultrasonic image display device having the display portion 10 integrally configured in the intra-operative goggle can be adopted.

As shown in FIG. 7A and FIG. 7B, a specific goggle 50 incorporated in an ultrasonic image display device having the display portion 10 integrally configured in the intra-operative goggle can be adopted.

In this case, a television format signal (or a RGB signal) and control signal cables 51 and 52 connected to the apparatus main body 20 are installed in the specific goggle 50. By switch operation of the keyboard, foot switch or the like, for example, via these cables 51 and 52, the display state of the display unit 10 in the specific goggle 50 can be controlled so that the ultrasonic 3D image is displayed during ON and can be controlled so as to restore to a normal viewing field during OFF.

Figure 8:
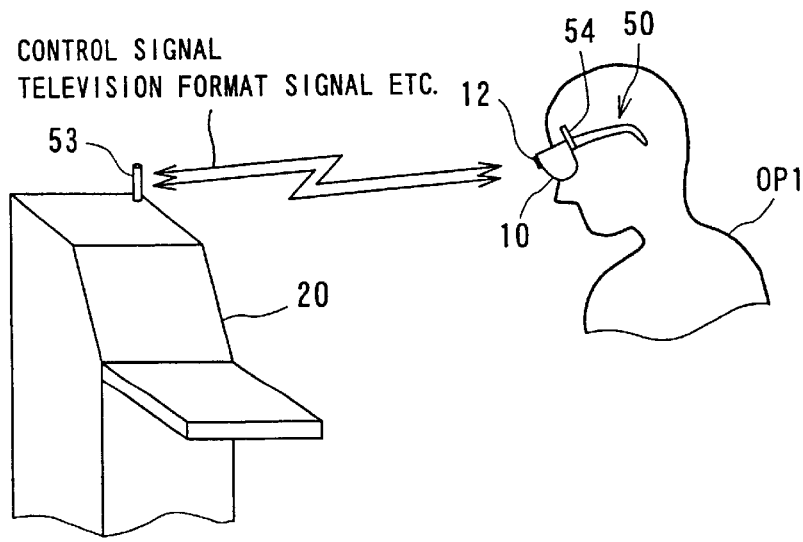
FIG. 8 is a schematic view showing another example of the intra-operative specific goggle incorporated in the display portion according to the present invention.

In the apparatus using the specific goggle 50 incorporated in the above ultrasonic image display device, as a modified example thereof, instead of cables 51 and 52, there may be, of course, provided wireless devices 53 and 54 having an antenna capable of communicating a television format signal (or an RGB signal) and a control signal or the like between the apparatus main body 20 and the specific goggle 50 in a wireless manner as shown in FIG. 8. The setting positions of these wireless devices 53 and 54 are not limited to the illustrative embodiment, and can be arbitrarily set as long as the above signals can be communicated in a wireless manner.

Figure 9:
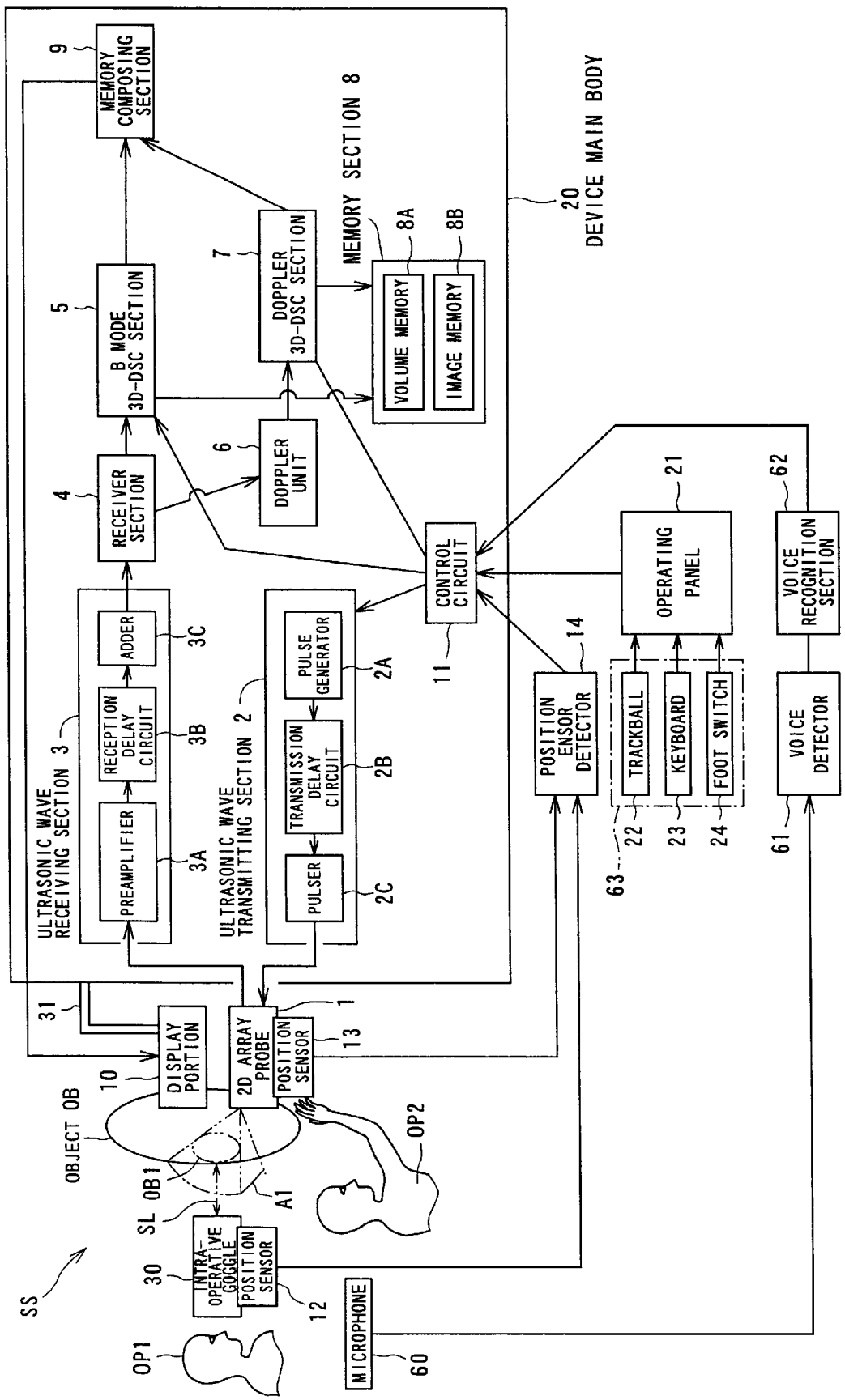
FIG. 9 is a schematic block diagram illustrating a configuration of an apparatus when a projection direction of a 3D image is changed according to the present invention.
Figure 10:
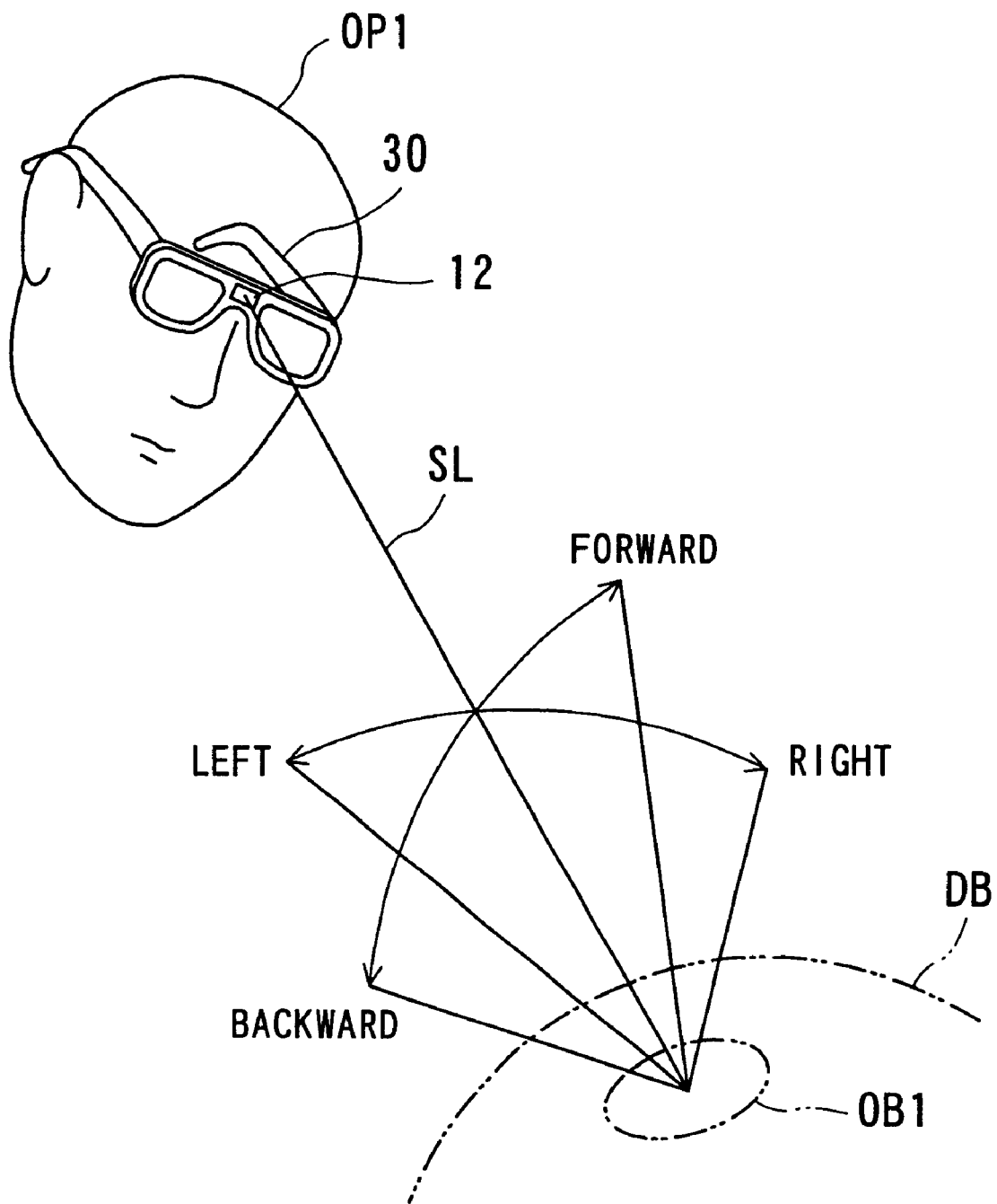
FIG. 10 is a conceptual view schematically illustrating an example when the projection direction of the 3D image is changed according to the present invention.

As another example, the embodiments shown in FIG. 9 and FIG. 10 are applicable. In addition to the construction similar to the above, the three-dimensional ultrasonic diagnosis apparatus in this embodiment, as shown in FIG. 9, comprises: a microphone (voice input device) 60 for inputting a voice such as operator's instruction (change of viewing direction or the like); a voice detector 61 for detecting a voice inputted by this microphone 60; a voice recognition section 62 for recognizing the operator's instruction from the voice detected by this voice detector 61; and a control circuit 11 for adding a projection direction changing function so that the projection direction SL of the 3D image is changed in a specific direction based on the operator's instruction recognized at this voice recognition section.

In a method for changing the projection direction SL in the control circuit 11, for example, as shown in FIG. 10, in the case where the field of interest OB1 of the object OB is seen from the first position sensor 12 mounted on the goggle 30, the 3D image projection direction SL may be frozen at a desired position of the operator OP1 while the direction is shifted to a side indicated in the right, left, forward, and backward sides by the indicated angle; or is shifted to the indicated side with predetermined time intervals by a predetermined angle.

The shifting direction in the projection direction can be set in an arbitrary direction without being limited thereto.

Means for recognizing the operator's instruction may be input means using an external input device such as trackball 22, keyboard 23, foot switch 24 or the like of the operating panel 21, for example, without being limited to means using the microphone 60, the voice detector 61 and the voice recognition section 62 described above.

Now, embodiments of the three-dimensional ultrasonic diagnosis apparatus according to the present invention as described above and an outline of the procedures mainly used in the intra-operative system SS in such each modified example will be described with reference to FIG. 11 to FIG. 14.

Figure 11:
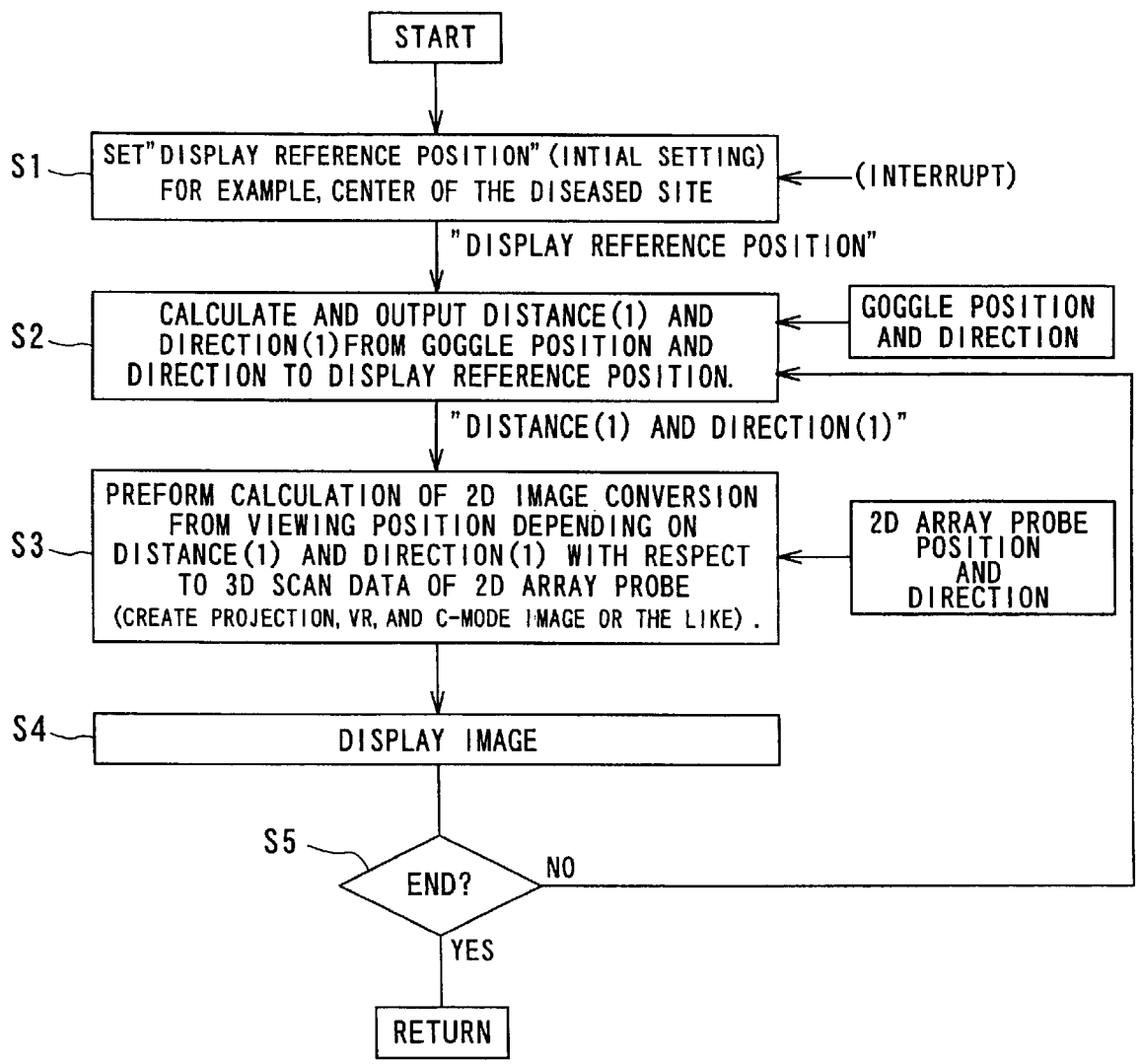
FIG. 11 is a flowchart showing a basic procedural example of the three-dimensional ultrasonic diagnosis apparatus according to the present invention.
Figure 12:
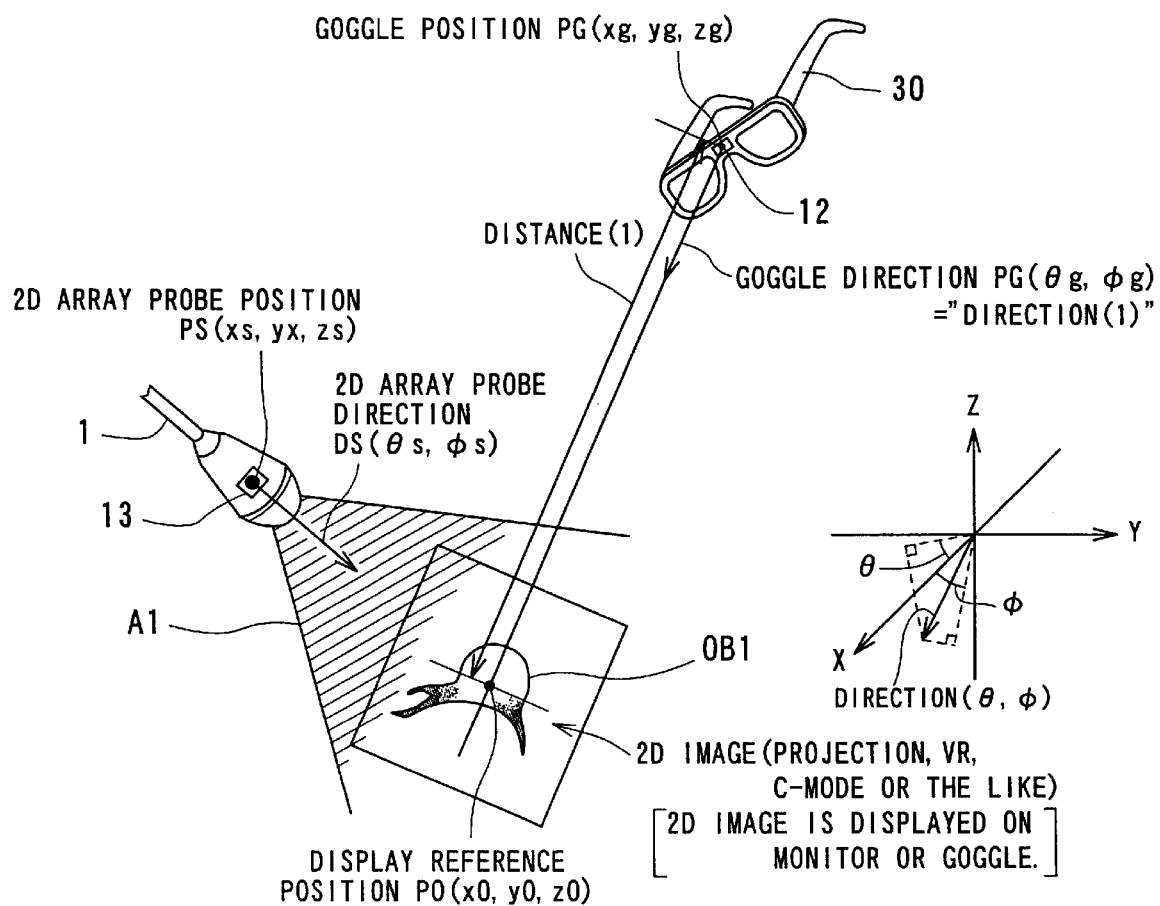
FIG. 12 is a conceptual view schematically illustrating a procedural example shown in FIG. 11 according to the present invention.

FIG. 11 illustrates the most basic procedures for the three-dimensional ultrasonic diagnosis apparatus; and FIG. 12 shows its outline. In FIG. 11, first, when intra-operative assistance using this apparatus is started, the processing in step S1 is performed. In this step S1, a display reference position P0 (x0, y0, z0) -on the display face PL shown in FIG. 12 is initially set at a center position of a diseased site, for example. The P0 can be newly changed by operator's manipulation during operation.

Next, in step S2, distance (1) and direction (1) (=DG) is calculated from the position PG (xg, yg, zg) and goggle direction DG (θg, φg) of the goggle 30 shown in FIG. 12 by means of a control circuit 11 (refer to FIG. 1 and FIG. 9). Here, the goggle position PG and the direction DG correspond to three-dimensional position information (the position vector and direction vector of the first position sensor 12) always inputted from the first position sensor 12 shown in FIG. 1 or the like, for example, to the control circuit 1 1 via the position sensor detecting section 14.

The thus calculated distance (1) and direction (1) are outputted, respectively, to the B mode 3D-DSC section 5 and Doppler 3D-DSC section 6 (refer to FIG. 1).

Then, in step S3, calculation of 2D image conversion from the viewing position to the display face PL depending on the distance (1) and direction (1) is performed for 3D data in the 3D scan area A1 for the 2D array probe 1 shown in FIG. 12, for example by means of the B mode 3D-DSC section 5 and the Doppler 3D-DSC section 6 (refer to FIG. 1 and FIG. 9). Here, the 3D data on the 3D scan area A1 is calculated at its three-dimensional position by means of the position vector and direction vector of the 2D array probe 1 always inputted from the second position sensor 13 shown in FIG. 1 or the like, for example, to the control circuit 11 via the position sensor detecting section 14. The position vector and direction vector of this 2D array probe 1 correspond to the position PS (xs, ys, zs) and direction DS (θs, φs) of the 2D array probe 1 shown in FIG. 12. A projection image, a VR image, a C-mode image or the like, for example are created by calculation of the above 2D -image conversion.

Then, in step S4, the projection image, VR image, and C-mode image or the like created by the above calculation are displayed on a monitor or a goggle by means of the display portion 10 (refer to FIG. 1, FIG. 2, FIG. 5A and FIG. 5B, and FIG. 7 to FIG. 9) via the memory composing section 9 (refer to FIG. 1 and FIG. 9), for example.

The processing in the above steps S2 to S4 is repeatedly executed until the end of processing has been judged in step S5. When a new display reference position is inputted, the processing in the above steps S2 to S4 is interrupted. In this manner, the new display reference position is set by returning to step S1, and then, the processing similar to the above is repeatedly executed.

The contents of the processing shown in FIG. 11 and FIG. 12 above is the most basic common to the embodiment of the three-dimensional ultrasonic diagnosis apparatus according to the present invention and each of the modified examples. The processing is not always limited thereto, and can be variously changed and implemented within the scope of the present invention.

Figure 13:
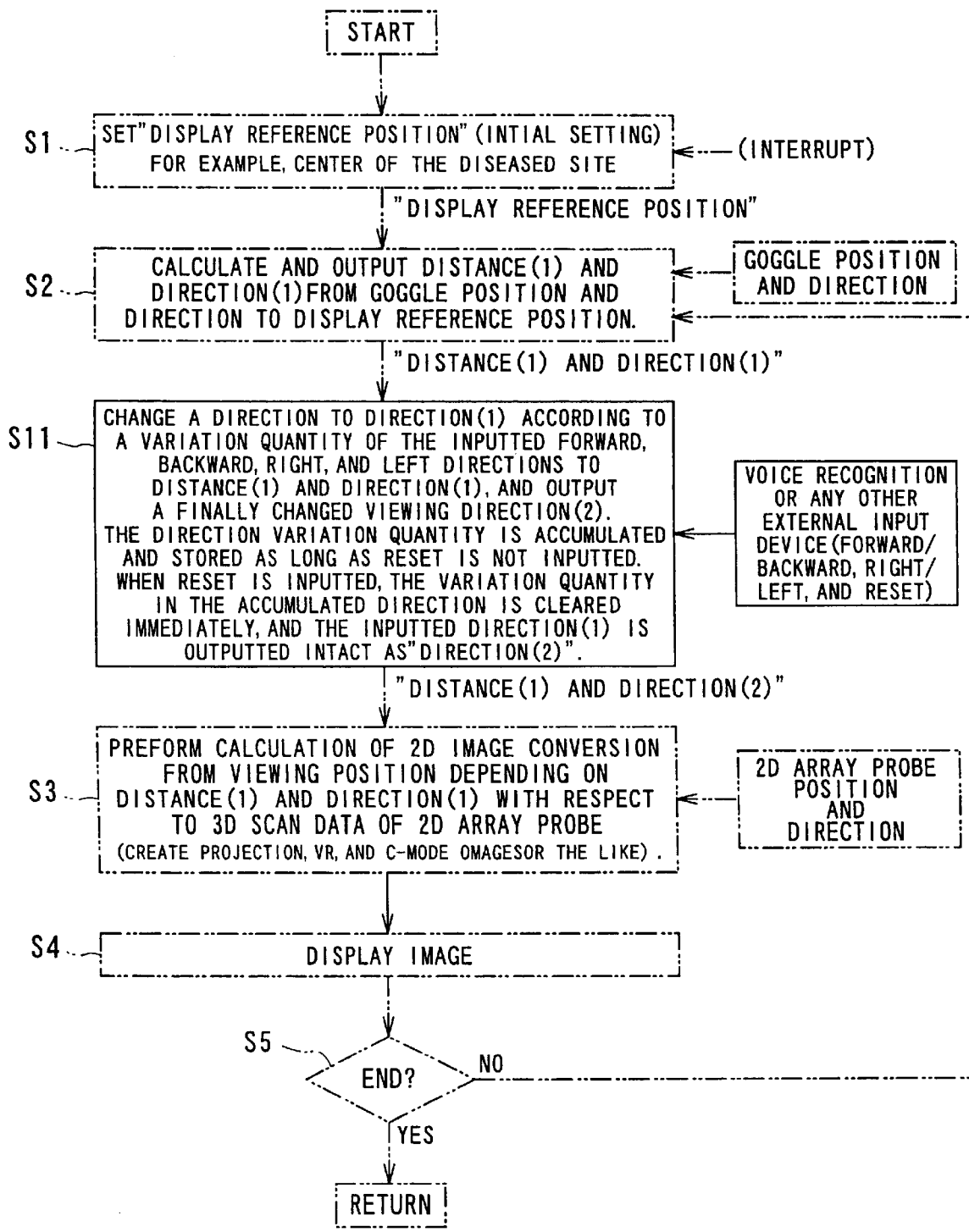
FIG. 13 is a flowchart illustrating a procedural example when the viewing position of the three-dimensional ultrasonic diagnosis apparatus is changed according to the present invention.
Figure 14:
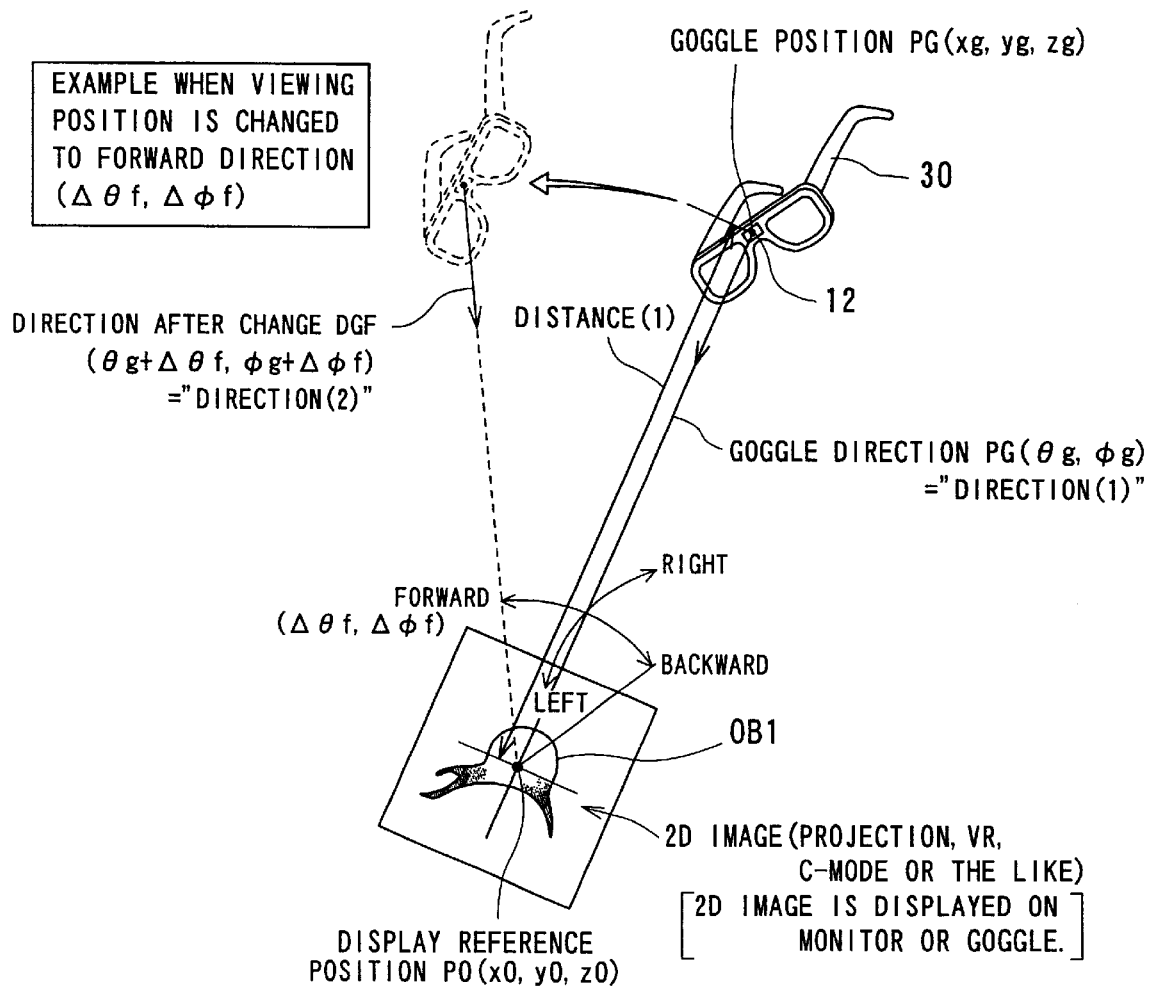
FIG. 14 is a conceptual view schematically illustrating a procedural example shown in FIG. 13 according to the present invention.

FIG. 13 illuminates an embodiment described in the aforementioned FIG. 9 and FIG. 10, i.e., the procedures employing an example for changing the viewing position. FIG. 14 shows its outline. In FIG. 14, there is shown an outline when a viewing position is changed to forward direction. A case in which the viewing direction is changed to the other direction can be applied similarly, and thus, it is not illustrated in particular.

The procedures shown in FIG. 13 is such that step S11 is inserted between steps S2 and S3 shown in the aforementioned FIG. 11 (hereinafter, the same step as processing shown in FIG. 11 is simplified or omitted). That is, in FIG. 13, by means of the control circuit 11 (refer to FIG. 9 or the like), the procedures in the aforementioned steps S1 and S2 are sequentially executed. For example, the distance (1) and direction (1) (=DG) are calculated and outputted from the position PG (xg, yg, zg) of the goggle 30 shown in FIG. 14 and the goggle direction DG (θg, φg) to the display reference position P0 (x0, y0, z0).

Next, in step S11, by means of the control means 11 (refer to FIG. 9 or the like), for example, the direction (1) (=DG (θg, φg) is changed to be a new direction DGF ((θg+Δθf φg+Δφf) according to a variation (Δθf, Δφf) in forward, backward, right, or left direction inputted to the distance (1) and direction (1) similar to the aforementioned ones shown in FIG. 14 via the aforementioned voice recognition means or any other external input device (refer to FIG. 9 or the like). Thus, the finally changed "viewing direction (2) (=(θg+Δθf, φg+Δφf))" is outputted. Here, the variation in each direction is assumed to be accumulated and stored as long as reset input is not made, for example. In this case, when reset input is made, the variation in the accumulated direction at that time is cleared immediately, and the inputted direction (1) is outputted intact as "direction (2)".

Then, in step S3, calculation of 2D image conversion from the viewing direction to the display face PL depending on the distance (1) and "direction (2)" is performed for 3D data of the 3D scan area A1 for the aforementioned 2D array probe 1 by the B mode 3D-DSC section 5 and Doppler 3D-DSC section 6 (refer to FIG. 1 and FIG. 9). Here, the 3D data on the 3D scan area A1 is calculated at its three-dimensional position by the position vector and direction vector of the 2D array probe 1 always inputted from the second position sensor 13 shown in FIG. 1 or the like, for example, to the control circuit 11 via the position sensor detecting section 14. The position vector and direction vector of this 2D array probe 1 correspond to the position PS (xs, ys, xs) and direction DS (θs, φs) shown in FIG. 12. The projection image, VR image, and C-mode image or the like, for example, are created by calculation of the above 2D image conversion.

Next, in step S4, 2D image such as the projection image, VR image, and C-mode image or the like created by the above calculation are displayed on a monitor or a goggle by means of the display portion 10 (refer to FIG. 2, FIG. 5A and FIG. 5B, and FIG. 7 to FIG. 9) via the memory composing section 9 (refer to FIG. 9 or the like), for example.

The processing in the above steps S2, S11, S3 and S4 is repeatedly executed until the end of processing has been judged in step S5. When a new display reference position is inputted, the processing in the above steps S2 to S4 is interrupted. In this manner, a new display reference position is set by returning to step S1, and thus, processing similar to the above is repeatedly executed.

The contents of the processing shown in the above FIG. 13 and FIG. 14 is basic when a viewing position is changed in the embodiments of the three-dimensional ultrasonic apparatus according to the present invention and in each of the modified examples. The processing is not always limited thereto, and can be changed variously and implemented within the scope of the present invention.

What is claimed is:

1. A three-dimensional ultrasonic diagnosis apparatus comprising:
   a two-dimensional ultrasonic probe configured to transmit ultrasonic beams toward an object and to receive ultrasonic echo signals therefrom;
   a volume data generator and memory configured to generate and store three-dimensional region volume data of the object based on the ultrasonic echo signals received by the ultrasonic probe in real time;
   a direction detector configured to detect direction data concerning an orientation of at least one of a head and a face of an operator;
   a display image generator configured to generate a two-dimensional display image in real time from the three-dimensional region volume data stored by the volume data generator and memory based on the direction data outputted from the direction detector; and
   a display configured to display the two-dimensional display image.

2. The three-dimensional ultrasonic diagnosis apparatus of claim 1, further comprising a controller configured to change a magnification of the two-dimensional display image according to a change in distance between (1) the at least one of the head and face of the operator and (2) a three-dimensional region in the object.

3. The three-dimensional ultrasonic diagnosis apparatus of claim 1, wherein the direction detector comprises:
- a first position sensor for detecting first position information concerning a viewpoint of the operator or a position depending on the viewpoint of the operator; and
- a second position sensor for detecting second position information concerning a position of the two-dimensional ultrasonic probe, wherein the display comprises:
- a view setting unit configured to set a specific projection direction whose reference is a viewing direction of the operator based on the first position information detected by the first position sensor and the second position information detected by the second position sensor; and
- a display unit configured to display three-dimensional anatomical information in the three-dimensional region for the object in real time when the three-dimensional volume image is seen in the specific projection direction set by the view setting means.

4. The three-dimensional ultrasonic diagnosis apparatus of claim 3, wherein the first sensor is mounted on at least one of intra-operative goggles and eyeglasses that the operator wears, and the second sensor is mounted on the two-dimensional ultrasonic probe.

5. The three-dimensional ultrasonic diagnosis apparatus of claim 3, wherein the first position sensor is a magnetic sensor.

6. The three-dimensional ultrasonic diagnosis apparatus of claim 3, wherein the display further comprises an arm device for movably installing the display portion in a region close to a field of interest of the object.

7. The three-dimensional ultrasonic diagnosis apparatus of claim 6, wherein the arm device comprises an arm main body and at least one joint section disposed at the arm main body, the joint section being rotatable at least in horizontal and vertical directions.

8. The three-dimensional ultrasonic diagnosis apparatus of claim 3, wherein the display further comprises a display portion rotator configured to cause the display portion to be rotated so that a display face of the display portion is automatically oriented to a side of the operator.

9. The three-dimensional ultrasonic diagnosis apparatus of claim 8, wherein the display further comprises a controller configured to control a display portion rotation movement using the display portion rotator based on position information from the first position sensor.

10. The three-dimensional ultrasonic diagnosis apparatus of claim 3, wherein the display unit is configured in intra-operative goggles that the operator wears.

11. The three-dimensional ultrasonic diagnosis apparatus of claim 10, wherein the display portion configured in the intra-operative goggles comprises an ON/OFF controller configured to control the display/non-display of an ultrasonic image using an ON/OFF function of a switch.

12. The three-dimensional ultrasonic diagnosis apparatus of claim 11, wherein the ON/OFF controller comprises means for controlling information concerning a normal field of vision during non-display of an ultrasonic image.

13. The three-dimensional ultrasonic diagnosis apparatus of claim 3, wherein the display further comprises:
- an instruction recognition unit configured to recognize an instruction from the operator; and
- a projection direction change unit configured to change a specific projection direction set by the view setting unit according to the instruction recognized by the instruction recognition unit.

14. The three-dimensional ultrasonic diagnosis apparatus of claim 13, wherein the instruction recognition unit comprises a voice recognition unit for recognizing the voice of the operator.

15. A three-dimensional ultrasonic diagnosis apparatus, comprising:
- a two-dimensional ultrasonic probe configured to transmit ultrasonic beams toward an object and to receive ultrasonic echo signals therefrom;
- a volume data generator and memory configured to generate and store three-dimensional region volume data of the object based on the ultrasonic echo signals received by the ultrasonic probe in real time;
- a direction detector configured to detect direction data concerning a viewing direction of an operator;
- a display image generator configured to generate a two-dimensional display image in real time from the three-dimensional region volume data stored by the volume data generator and memory based on the direction data outputted from the direction detector; and
- a display configured to display the two-dimensional display image.

* * * * *